United States Patent [19]

Krespan et al.

[11] Patent Number: 4,922,038

[45] Date of Patent: May 1, 1990

[54] PREPARATION OF 1,1,1,2-TETRAFLUORODICHLOROETHANE

[75] Inventors: Carl G. Krespan; Bruce E. Smart, both of Wilmington, Del.

[73] Assignee: E. I. DuPont de Nemours and Company, Wilmington, Del.

[21] Appl. No.: 303,152

[22] Filed: Jan. 30, 1989

[51] Int. Cl.$^5$ .................. C07C 17/00; C07C 17/04
[52] U.S. Cl. ............................................. 570/175
[58] Field of Search ............... 570/175, 166, 170, 123, 570/124

[56] References Cited

U.S. PATENT DOCUMENTS 3,231,519  1/1966  Clark et al. .................. 252/462

OTHER PUBLICATIONS

Vecchio et al., J. Flourine Chem., 4 (1974), pp. 117–139.
C. G. Krespan, J. of Organic Chemistry, 27, 1813 (1962).

Primary Examiner—Donald B. Moyer
Assistant Examiner—Tracy S. Hanna

[57] ABSTRACT

This invention provides for a process for the preparation of 1,1,1,2-tetrafluorodichloroethane (FC-114a) by reacting $CF_2=CFCl$ in a polar aprotic solvent with a source of fluoride ion selected from at least one alkali metal fluoride and/or at least one tetraalkylammonium fluoride and with a source of chlorine selected from at least one of $CCl_4$, $CCl_3CCl_3$, and $CCl_3CCl_2CCl_3$ at a temperature from about 25° C. to about 150° C.

7 Claims, No Drawings

PREPARATION OF 1,1,1,2-TETRAFLUORODICHLOROETHANE

FIELD OF THE INVENTION

Process for the preparation of 1,1,1,2-tetrafluorodichloroethane (FC-114a) by reacting $CF_2=CFCl$ in a polar aprotic solvent with a source of fluoride ion and a source of chlorine.

BACKGROUND OF THE INVENTION

A variety of processes which produce FC-114a are known in the art. Representative of these include U.S. Pat. No. 3,231,519 which discloses the preparation of a mixture of 1,2-dichlorotetrafluoroethane (FC-114) and 114a by reacting 1,1,2-trichlorotrifluoroethane (FC-113) with HF in the presence of a catalyst. This process produces more than twice as much FC-114 as it does FC-114a.

Vecchio et al., J. Fluorine Chem., 4 (1974) 117–139, discloses a high temperature fluorination of hexachloroethane or tetrachloroethylene and $Cl_2$ with HF in the presence of an aluminum fluoride catalyst to produce FC-114a and 1,1,1-triclorotrifluoroethane (FC-113a). In this process FC-114a was produced in 41 mole percent and FC-113a in 20 mole percent, the remainder being unreacted starting material and other fluorination products.

There is growing demand for environmentally desirable fluorocarbons for use as solvents, blowing agents and, particularly, refrigerants. One suitable fluorocarbon particularly useful as a refrigerant is 1,1,1,2-tetrafluoroethane (FC-134a). FC-114a is highly useful as an intermediate in the production of FC-134a. This invention provides a process for producing FC-114a with high selectivity.

SUMMARY OF THE INVENTION

This invention provides for a process for the preparation of 1,1,1,2-tetrafluorodichloroethane (FC-114a) by reacting $CF_2=CFCl$ in a polar aprotic solvent with a source of fluoride ion selected from at least one alkali metal fluoride and/or at least one tetraalkylammonium fluoride and with a source of chlorine selected from at least one of $CCl_4$, $CCl_3CCl_3$, and $CCl_3CCl_2CCl_3$ at a temperature from about 25° C. to about 150° C.

DETAILS OF THE INVENTION

Polar aprotic solvents useful in the practice of this invention are well known in the art and include dimethylformamide, dimethylacetamide, N-methylpyrrolidinone, dimethyl sulfoxide, acetonitrile, 1,2-dimethoxyethane, and diethylene glycol dimethyl ether.

Alkali metal fluorides useful in the practice of this invention include Na, K, Rb and Cs fluoride. Lithium fluoride is not recommended for use, because of its poor reactivity. Of the useful metal fluorides reactivity increases from Na to Cs. Potassium fluoride is preferred for a combination of reactivity and economics. The tetraalkylammonium fluorides useful in the practice of this invention include compounds of the formula $R_4NF$ where R is at least one selected from saturated hydrocarbyls of the formula $C_nH_{2n+1}$ where n=1 to 20. Preferred for economics and availability are tetramethylammonium fluoride (n=1) and tetraethylammonium (n=2) fluoride.

The source of chlorine preferred for economics is $CCl_4$.

The process of the invention can be practiced at a temperature from about 25° C. to about 150° C., and, preferably, from about 100° C. to about 125° C.

Pressure is not particularly critical and can vary from atmospheric pressure (1 atm) to 30 atm. Pressures from 5 to 20 atm are preferred for a combination of convenience and short reaction times.

The reaction vessel utilized in the practice of this invention is not critical. Any reaction vessel capable of withstanding the chosen pressure can be used. Metal reaction vessels are preferred for convenience and pressure tolerance.

Reaction time is not particularly critical and varies with temperature. The reaction can generally be run from 0.5 minutes to 20 hours.

Under the process conditions of this invention the FC-114a can be isolated from the reaction mixture by simple fractional distillation, because the boiling point of the polar aprotic solvents utilized is significantly different from that of FC-114a.

EXAMPLES

In the following illustrative examples, all parts and precentages are by weight and all temperatures are Centigrade unless otherwise stated. All reactions use commercially available starting materials.

EXAMPLE 1

A mixture of 29 grams (0.50 mol) of oven-dried potassium fluoride, 60 grams (0.25 mol) of hexachloroethane, 150 mL of dimethylformamide, and 29 grams (0.25 mol) of chlorotrifluoroethylene was heated in a metal tube at 100° for 12 hours. Volatile materials, 30.9 grams, which distilled from the warm reaction mixture were analyzed by Gas Chromatograph/Mass Spectrometer. The volatile materials were found to consist essentially of 6.6 grams of 1,1,1,2-tetrafluorodichloroethane (15% conversion, 91% yield), 24 grams (83% recovery) of unreacted chlorotrifluoroethylene and 0.3 gram of other fluorinated materials.

EXAMPLE 2

The procedure of Example 1 was followed except that 150 mL of acetonitrile was used instead of the dimethylformamide and the reaction mixture was heated for 6 hours at 100°, then for 6 hours at 125°. The volatile materials, 9.5 grams, were found to consist essentially of 1.9 grams of 1,1,1,2-tetrafluorodichloroethane (4% conversion), the remainder consisting essentially of unreacted chlorotrifluoroethylene and other fluorinated materials.

What is claimed:

1. A process for the preparation of 1,1,1,2-tetrafluorodichloroethane comprising reacting $CF_2=CFCl$ in a polar aprotic solvent with a source of fluoride ion selected from at least one alkali metal fluoride and/or at least one tetraalkylammonium fluoride and with a source of chlorine selected from at least one of $CCl_4$, $CCl_3CCl_3$, and $CCl_3CCl_2CCl_3$ at a temperature from about 25° C. to about 150° C., and recovering said 1,1,1,2-tetrafluorodichloroethane from the reaction mixture.

2. The process of claim 1 wherein the temperature is from about 100° C. to about 125° C.

3. The process of claim 1 wherein the alkali metal fluoride is selected from at least one of Na, K, Rb and Cs fluoride.

4. The process of claim 3 wherein the alkali metal fluoride is potassium fluoride.

5. The process of claim 1 wherein the tetraalkylammonium fluoride is a compound of the formula $R_4NF$ where R is at least one selected from saturated hydrocarbyls of the formula $C_nH_{2n+1}$ where n = 1 to 20.

6. The process of claim 5 wherein n = 1 to 2.

7. The process of claim 1 wherein the source of chlorine is $CCl_4$.

* * * * *